US011415517B1

(12) United States Patent
Meyer et al.

(10) Patent No.: US 11,415,517 B1
(45) Date of Patent: Aug. 16, 2022

(54) UNWANTED NEAR-INFRARED SIGNAL SUPPRESSION

(71) Applicant: KARL STORZ Imaging, Inc., Goleta, CA (US)

(72) Inventors: William H. Meyer, Ventura, CA (US); Jonathan Bormet, Goleta, CA (US)

(73) Assignee: KARL STORZ Imaging, Inc., Goleta, CA (US)

( * ) Notice: Subject to any disclaimer, the term of this patent is extended or adjusted under 35 U.S.C. 154(b) by 0 days.

(21) Appl. No.: 17/198,122

(22) Filed: Mar. 10, 2021

(51) Int. Cl.
*G01N 21/64* (2006.01)
*A61B 5/00* (2006.01)

(52) U.S. Cl.
CPC ....... *G01N 21/6486* (2013.01); *A61B 5/0071* (2013.01); *G01N 21/6458* (2013.01)

(58) Field of Classification Search
CPC ............ G01N 21/6486; G01N 21/6458; A61B 5/0071
See application file for complete search history.

(56) References Cited

U.S. PATENT DOCUMENTS

2008/0039715 A1* 2/2008 Wilson ...................... A61B 5/06
   600/424
2018/0310829 A1* 11/2018 Frangioni .............. A61B 34/20

FOREIGN PATENT DOCUMENTS

EP    3343912 A1    7/2018

* cited by examiner

*Primary Examiner* — Hugh Maupin
(74) *Attorney, Agent, or Firm* — Michael Loi

(57) ABSTRACT

An enhanced fluorescence imaging system includes a light source for emitting non-visible and visible light and a visible light image sensor and a non-visible light image sensor. Each pixel of the visible light image sensor corresponds to a pixel of the non-visible light image sensor. Data processing hardware performs operations that include, for each pixel in the visible light image sensor, determining an intensity of visible light received by the pixel. The operations also include determining, based on the intensity, an amount of unwanted non-visible light captured by the corresponding pixel of the non-visible light image sensor. The unwanted non-visible light originates from sources other than the non-visible light source. The operations also include reducing an intensity of non-visible light in non-visible image data captured by the corresponding pixel based on the determined amount of unwanted non-visible light.

26 Claims, 7 Drawing Sheets

| VL Intensity 220 | NVL Correction Value 230 |
|---|---|
| 10 | 0.2 |
| 20 | 0.4 |
| 30 | 0.6 |
| 40 | 0.8 |
| . . . . | . . . . |
| 100 | 2 |
| . . . . | . . . . |
| 1000 | 20 |

FIG. 2A

UNWANTED NEAR-INFRARED SIGNAL SUPPRESSION

TECHNICAL FIELD

The disclosure relates to a fluorescence imaging system for medical procedures.

BACKGROUND

Endoscopes are commonly used to provide access to body cavities while decreasing the invasiveness of a surgical procedure. A fluorescence imaging system can include an endoscope, one or more light sources that emit both visible (e.g., white) light and non-visible (e.g., infrared) light, a camera control unit, and a display control unit. The visible light is typically used as a reference light or illuminating light, while the non-visible light is typically used as an excitation light. That is, the non-visible light may be used to irradiate a fluorescent substance (e.g., dye) administered to a patient or certain tissues and/or fluids of the body, which in turn causes the fluorescent substance or tissues and/or fluids to emit fluorescence light. The endoscope includes one or more image sensors to capture the reflected visible light and/or the emitted fluorescence light. The fluorescence imaging system may overlay a visual representation of non-visible light onto the visible light image.

However, viewing the fluorescing image data or combining or mixing the image data may result in instances where the non-visible light component is too pronounced, too light, too diffuse, or too discolored. In particular, non-visible light is attendant with illuminating light and a signature of the non-visible light increases with the intensity of the illuminating light. As such, it is desirable to eliminate or reduce unwanted non-visible light resulting from the illuminating light.

SUMMARY

One aspect of the disclosure provides an imaging system for use in a medical procedure. The imaging system includes a first light source (or other visible light source) for emitting visible light. The system also includes a second light source (or other non-visible light source) for emitting non-visible light, such as infrared light. The system also includes a first image sensor for capturing visible light image data in the visible light spectrum. The system also includes a second image sensor for capturing non-visible light image data in the non-visible light spectrum. Each pixel of the first image sensor corresponds to a pixel of the second image sensor. The system also includes data processing hardware in communication with the first image sensor and the second light image sensor and memory hardware in communication with the data processing hardware. The memory hardware stores instructions that when executed on the data processing hardware cause the data processing hardware to perform operations. The operations include, for each pixel in the first image sensor, determining an intensity of visible light received by the pixel of the first image sensor. The operations also include determining, based on the intensity of visible light received by the pixel of the first image sensor, an amount of unwanted non-visible light captured by the corresponding pixel of the second image sensor. The unwanted non-visible light originates from sources other than the second light source and the emission from the target due to the excitation by the second light source. The operations also include reducing an intensity of unwanted non-visible light in the non-visible light image data captured by the corresponding pixel of the second image sensor based on the determined amount of unwanted non-visible light, so as to provide accurate image data for each pixel of the second image sensor.

Implementations of the disclosure may include one or more of the following optional features. In some implementations, the operations further include determining a threshold for the intensity of visible light received by the pixel of the first image sensor. In this implementation, determining the amount of unwanted non-visible light captured by the corresponding pixel of the second image sensor is based on the threshold for the intensity of visible light received by the pixel of the first image sensor.

In some examples, determining the amount of unwanted non-visible light captured by the corresponding pixel of the second image sensor includes determining an amount that the intensity of visible light exceeds the threshold for the pixel of the first image sensor. Reducing the intensity of the non-visible light in the non-visible light image data captured by the corresponding pixel of the second image sensor based on the determined amount of unwanted non-visible light may include reducing the intensity of non-visible light in the non-visible light image data captured by the corresponding pixel of the second image sensor based on the amount that the intensity of visible light exceeds the threshold for the pixel of the first image sensor. Optionally, determining the amount of unwanted non-visible light captured by the corresponding pixel of the second image sensor includes obtaining, from a lookup table, the amount of unwanted non-visible light based on the intensity of visible light received by the pixel of the first image sensor that corresponds to one of the plurality of values of visible light intensity.

Optionally, the threshold for the intensity of visible light received by the pixel of the first image sensor is at a saturation level. In some examples, the threshold for the intensity of visible light received by the pixel of the first image sensor is based on at least one parameter of the imaging system. The at least one parameter may include at least one selected from the group of (i) an amount of glass of the imaging system, (ii) a type of glass of the imaging system, (iii) a type of adhesive of the imaging system, and (iv) a type of the first light source.

In some implementations, the operations further include, for each pixel in the second image sensor, determining a difference between the intensity of non-visible light received by the pixel of the second image sensor when the second light source is enabled and when the first source is disabled or when the second light source is disabled and when the first light source is enabled. The operations may also further include updating the determined threshold for the intensity of visible light received by the pixel of the first image sensor based on the measured difference.

Determining the threshold for the intensity of visible light received by the pixel of the first image sensor may include processing, using a model, the non-visible light image data and the visible light image data based on a geometry of a scene captured by the imaging system. The model may be a neural network. Reducing the intensity of non-visible light captured by the corresponding pixel of the second image sensor based on the determined amount of unwanted non-visible light may include reducing the intensity of non-visible light received by the corresponding pixel of the second image sensor proportionally based on the intensity of visible light received by the pixel of the first image sensor. Optionally, the first image sensor and the second image sensor are co-sited.

Another aspect of the disclosure provides a method for suppressing unwanted non-visible light in an imaging system including a first light source, a second light source, a first image sensor configured to capture visible light image data, and a second image sensor configured to capture non-visible light image data. The imaging system is configured to generate a video image onto a display. The method includes, for each pixel in the first image sensor, determining an intensity of visible light received by the pixel of the first image sensor. The method also includes determining, based on the intensity of visible light received by the pixel of the first image sensor, an amount of unwanted non-visible light captured by the corresponding pixel of the second image sensor. The unwanted non-visible light originates from sources other than the second light source and the fluorescent emission form the target due to the excitation by the second light source. The method also includes reducing an intensity of non-visible light in the non-visible image data captured by the corresponding pixel of the second image sensor based on the determined amount of unwanted non-visible light, so as to provide accurate image data for each pixel of the second image sensor.

This aspect may include one or more of the following optional features. In some implementations, the method further includes determining a threshold for the intensity of visible light received by the pixel of the first image sensor. In this implementation, determining the amount of unwanted non-visible light captured by the corresponding pixel of the second image sensor is based on the threshold for the intensity of visible light received by the pixel of the first image sensor.

In some examples, determining the amount of unwanted non-visible light captured by the corresponding pixel of the second image sensor includes determining an amount that the intensity of visible light exceeds the threshold for the pixel of the first image sensor. Reducing the intensity of the non-visible light in the non-visible light image data captured by the corresponding pixel of the second image sensor based on the determined amount of unwanted non-visible light may include reducing the intensity of non-visible light in the non-visible light image data captured by the corresponding pixel of the second image sensor based on the amount that the intensity of visible light exceeds the threshold for the pixel of the first image sensor. Optionally, determining the amount of unwanted non-visible light captured by the corresponding pixel of the second image sensor includes obtaining, from a lookup table, the amount of unwanted non-visible light based on the intensity of visible light received by the pixel of the first image sensor that corresponds to one of the plurality of values of visible light intensity.

Optionally, the threshold for the intensity of visible light received by the pixel of the first image sensor is at a saturation level. In some examples, the threshold for the intensity of visible light received by the pixel of the first image sensor is based on at least one parameter of the imaging system. The at least one parameter may include at least one selected from the group of (i) an amount of glass of the imaging system, (ii) a type of glass of the imaging system, (iii) a type of adhesive of the imaging system, and (iv) a type of the first light source.

In some implementations, the method further includes, for each pixel in the second image sensor, determining a difference between the intensity of non-visible light received by the pixel of the second image sensor when the second light source is enabled and when the first light source is disabled. The method may also further include updating the determined threshold for the intensity of visible light received by the pixel of the first image sensor based on the measured difference.

Determining the threshold for the intensity of visible light received by the pixel of the first image sensor may include processing, using a model, the non-visible light image data and the visible light image data based on a geometry of a scene captured by the imaging system. The model may be a neural network. Reducing the intensity of non-visible light captured by the corresponding pixel of the second image sensor based on the determined amount of unwanted non-visible light may include reducing the intensity of non-visible light received by the corresponding pixel of the second image sensor proportionally based on the intensity of visible light received by the pixel of the first image sensor. Optionally, the first image sensor and the second image sensor are co-sited.

The details of one or more implementations of the disclosure are set forth in the accompanying drawings and the description below. Other aspects, features, and advantages will be apparent from the description and drawings, and from the claims.

BRIEF DESCRIPTION OF THE DRAWINGS

The embodiments set forth in the drawings are illustrative and exemplary in nature and not intended to limit the subject matter defined by the claims. The following description of the illustrative embodiments can be understood when read in conjunction with the following drawings, where like structure is indicated with like reference numerals and in which:

FIG. 2A is an example of a look-up table showing the unwanted non-visible light correction corresponding to the intensity of the visible light.

DETAILED DESCRIPTION OF PREFERRED EMBODIMENTS

Figure 1:
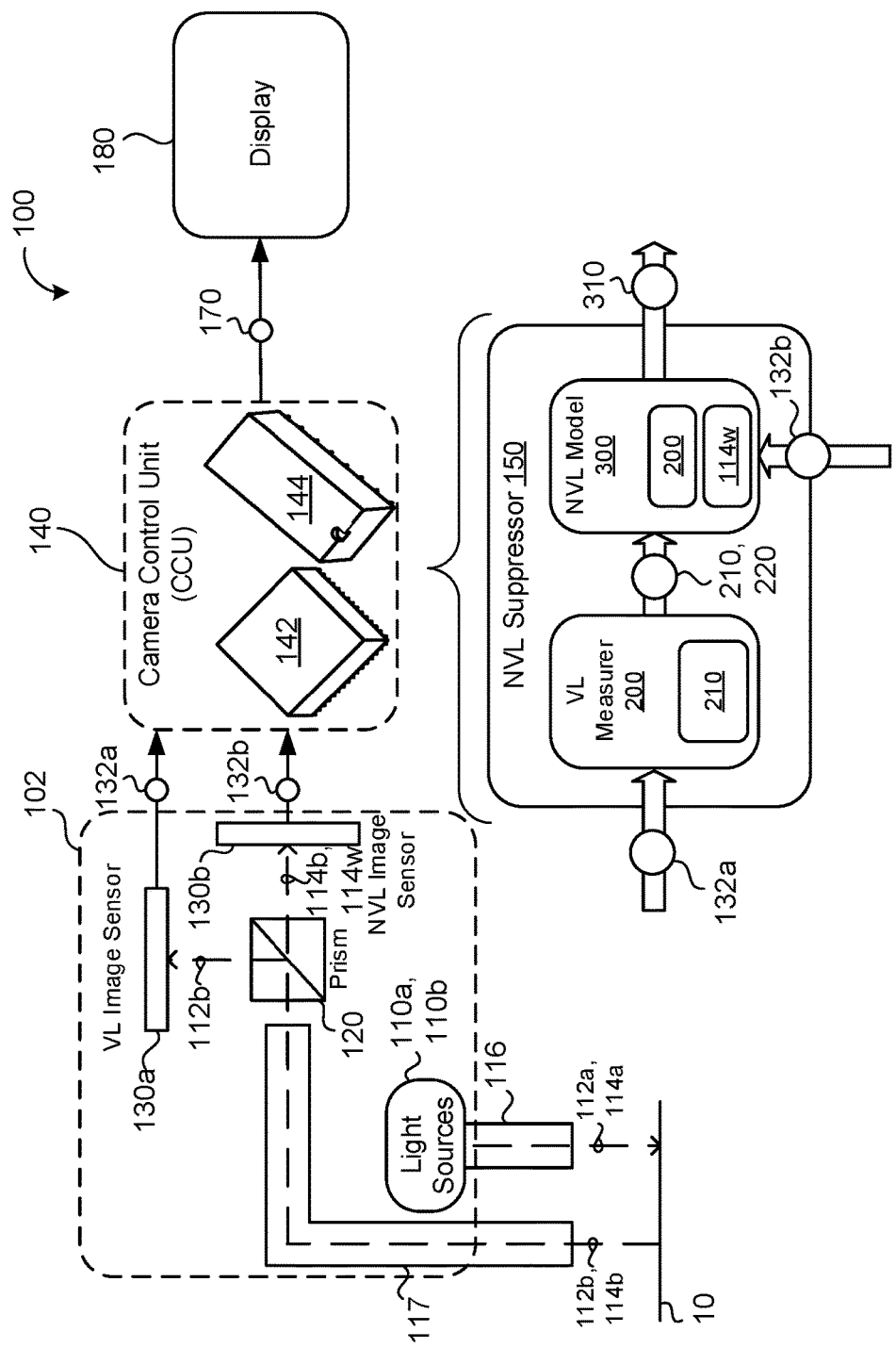
FIG. 1 is a schematic view of an example system for enhanced imaging.

Implementations herein are directed toward an enhanced imaging system that includes a first imaging sensor that captures visible light data and a second imaging sensor that captures non-visible light data. The system determines an amount of unwanted non-visible light in the image data captured by the second imaging sensor. The unwanted non-visible light may include non-visible light emitted by sources other than the non-visible light source and the emission from the target (e.g., by the visible light source and/or light delivery components). The system reduces an intensity of the non-visible light in the non-visible image data based on the amount of unwanted non-visible light.

Many devices, such as medical tools, include imaging equipment that captures visible white light images. For example, endoscopes include, in their most basic form, a rigid or a flexible tube with a light source and a camera. The flexible tube is passed through an orifice (e.g., the mouth) of a patient and the camera records images illuminated by the light. Endoscopes may include optical endoscopes with lens relay systems to transmit the image to the camera or video endoscope with no lens relay systems in which the camera may receive the image more directly.

In addition to visible white light, many imaging systems (such as endoscope systems) are capable of emitting other spectrums of light (i.e., non-visible light). For example, it is common for endoscope systems to also emit infrared light to support fluorescent imaging. The infrared light is absorbed by fluorescent dye, which in turn fluoresces. As used herein, the term "fluorescent dye" refers to dye approved for medical use, such as injection into tissue or the blood stream, and that is configured to absorb infrared light and in response, fluoresce, such as Indocyanine Green (ICG). ICG has a peak spectral absorption in the near infrared spectrum at approximately 800 nm. ICG, when irradiated with light between 750 nm and 950 nm, emits light (fluoresces) in another range of the spectrum. After irradiating the tissue with the near infrared light, the camera detects and images this fluorescence in order to provide an image to, for example, a display that visually indicates both the visible light and the non-visible light. For example, the endoscope system may covert the non-visible light to a select color and overlay the select color representative of the non-visible light over the visible light image.

Endoscopes may be equipped with one or more image sensors to image both white (i.e., visible) light and infrared (i.e., non-visible) light. For example, some endoscopes are equipped with a visible light image sensor (e.g., a white light image sensor) that captures visible light emitted by a visible light source and reflected back to the sensor and a non-visible light image sensor (e.g., an infrared image sensor) that captures non-visible light emitted from dye in tissue that has been excited by a non-visible light source. Ideally, the non-visible light captured by the non-visible image sensor is emitted only via excitation of the dye. However, in practice, small amounts of unwanted non-visible light emitted by sources other than the fluorescent dye are captured by the non-visible light sensor. For example, the visible light source and light delivery components emit small amounts of non-visible light (the "unwanted non-visible light"). This unwanted non-visible light may coincide with the wavelengths emitted by the fluorescing dye (e.g., ICG) and degrade the quality of the image captured by the non-visible image sensor. For example, the image may be too pronounced, too light, too diffuse, or too discolored due to the unwanted non-visible light.

For illustrative purposes, a description of a fluorescence image enhancer is provided within the context of an endoscopic system 100 or other imaging system. However, it should be appreciated that the fluorescence image enhancer may be utilized in other applications, illustratively including an exoscope, borescopes, videoscopes and other systems having two or more illumination-types and one or more image sensors. Furthermore, although the system 100 is described with respect to medical applications using fluorescing dye, it should be understood that industrial applications using other combinations of visible light and non-visible light may also benefit from the same principles.

Referring to FIG. 1, in some implementations, an example of an endoscopic system 100 (e.g., a fluorescence imaging system) includes a visible light source 110a and a non-visible light source 110b. The visible light source 110a emits visible light (VL) 112a (e.g., white light) and the non-visible light source 110b emits non-visible light (NVL) 114a (e.g., infrared light (IR), near-infrared (NIR) light, etc.). Typically, the light sources 110a, 110b simultaneously emit VL 112a and NVL 114a. However, the endoscopic system 100 may include the ability to alternate or switch between emitting VL 112a and NVL 114a. The VL 112a illuminates a scene (e.g., a surgical site) for the system 100. Both light sources 110a, 110b may include one or more light-emitting diodes (LEDs) or any other appropriate light-emitting device. In some examples, the light sources 110a, 110b are included within a camera head unit 102.

Light 112a, 114a emitted by the light sources 110a, 110b travels along a light guide 116 (e.g., an optical fiber or some lens system) and, after exiting the light guide 116, illuminates or irradiates a target area 10 (e.g., an internal cavity of a patient). Reflected VL 112b (i.e., VL 112a that has reflected from the target area 10) and, for example, emitted NVL 114b (e.g., fluorescent light (FL) emitted by, for example, ICG that has been irradiated by NVL light 114a or any other form of non-visible light) is directed back through an image relay 117 to, for example, a dichroic prism 120. The dichroic prism 120 splits received light into two beams of differing wavelength. That is, the dichroic prism 120 splits the received light, which may include reflected VL 112b and/or NVL 114b, to image sensors 130. The image sensors 130 may include a VL image sensor 130a (e.g., a white light image sensor) and an NVL image sensor 130b (e.g., an IR, an NIR, and/or a fluorescent light image sensor). For example, any reflected VL 112b (i.e., visible light) that passes through the prism 120 may be directed to the VL image sensor 130a, while any NVL 114b that passes through the prism 120 may be directed to the NVL image sensor 130b (i.e., light with a wavelength between 800 nm and 1200 nm). In some examples, the prism 120 and image sensors 130 are also included within the camera head unit 102. While a dichroic prism and two separate image sensors 130a, 130b are illustrated, any means for capturing image data representative of both the reflected VL 112b and NVL 114b is within the spirit and scope of the appended claims including, for example a single image sensor that captures both VL 112b and NVL 114b.

The image sensors 130 are typically fixed in place and the prism 120 directs light toward each sensor 130. The placement of the sensors 130 is generally very precise to keep the visible light and non-visible light spatially aligned (i.e., the sensors must be placed exactly where the prism directs the light). That is, the sensors 130 are co-sited such that each pixel of the VL image sensor 130a has a corresponding pixel of the NVL image sensor 130b. In this manner, when VL 112b and NVL 114b reflect from the same location, the corresponding pixels of the VL image sensor 130a and the NVL image sensor 130b will each capture the corresponding light 112b, 114b from the same portion of the target area 10.

The image sensors 130 may be a complementary metal oxide semiconductor (CMOS) or a Charged Coupled Device (CCD). It should be appreciated that any pixelated image sensor 130 currently known or later developed may be modified and adopted for use herein. The image sensors 130, in some implementations, include color filter arrays (CFAs). In some examples, the VL image sensor 130a and the NVL image sensor 130b are different sensors with the same or different resolutions. In other examples, the image sensors 130 are identical sensors. Identical sensors (e.g., the same resolution, geometry, etc.) often improve and ease manufacturing, assembly, and alignment of the system 100. In yet other examples, a single image sensor captures both reflected VL 112b and NVL 114b.

With continued reference to FIG. 1, the sensors 130 transmit VL image data 132a and NVL image data 132b to a camera control unit (CCU) 140. The CCU 140 may, in some examples, be included within the camera head unit 102, while in other examples is remote from the camera head unit 102. The CCU 140 includes computing resources 142 (e.g., data processing hardware) and storage resources 144 (e.g., memory hardware). In some implementations, the CCU 140 is disposed physically at the system 100 (e.g., within the camera head unit 102) and in wired communication with the image sensors 130. In other implementations, the CCU 140 is in wireless communication with the image sensors 130 (e.g., via wireless, Bluetooth, etc.) and may be remote from the image sensors 130 and/or system 100. In this case, the CCU 140 may correspond to any appropriate computing device 500 (see FIG. 5), such as a desktop workstation, laptop workstation, or mobile device (e.g., smart phone or tablet). In yet other implementations, the image data 132 may be stored in nonvolatile storage at the system 100 (e.g., a thumb drive) and later removed to be processed at data processing and memory hardware 142, 144 remote from the image sensors 130.

VL image data 132a received by the CCU 140, in some implementations, includes data for a plurality of pixels in an RGB format. The RGB format or color model is an additive color model that represents all colors via three chromaticities of three colors: red, green, and blue. Each pixel of the VL image data 132a has a corresponding intensity that indicates an intensity of the VL 112b received by the respective pixel. For example, when a pixel is exposed to greater intensity (i.e., brighter) VL 112B, the corresponding intensity value of the VL image data 132a is higher and when a pixel is exposed to lower intensity (i.e., dimmer) VL 112B, the corresponding intensity value of the VL image data 132a is lower. Similarly, each pixel of the NVL image data 132b has a corresponding intensity that indicates an intensity of the NVL 114b received by the respective pixel.

Ideally, the CCU 140 processes frames of the VL image data 132a for display on a display 180. Frames of image data captured by the VL image sensor 130a provide an image or video of a scene illuminated by the VL 112b. For example, the frames of VL image data may include a scene of an internal body cavity of a patient. Likewise, the CCU 140 processes frames of the NVL image data 132b for display on the display 180. The frames of NVL image data provide an image or video of NVL 114b of a scene. For example, the frames of NVL image data may depict light emitted by ICG that has been irradiated by NVL 114a. The CCU 140 may combine the frames of VL image data and frames of NVL image data to create a composition image 170 for display on the display 180. As an example, the NVL image data may be overlaid onto the VL image data. Alternatively, the display 180 displays frames of VL image data and NVL image data separately (e.g. side-by-side or Picture-in-Picture). Regardless, the displayed images allow a viewer to view both a scene illuminated by VL 112b and emitted NVL 114b (such as from dyes used in medical diagnostics).

However, the frames of NVL image data commonly have some amount of unwanted NVL (e.g., NIR energy) due to white light illumination, generation, and transmission to the scene. Glass formulations, adhesives, epoxies, and other materials used in the system may contribute to this unwanted NVL. For example, conventional white LEDs operating at a low intensity generate a small but detectable amount of MR energy. Additionally, light guides may exhibit an auto-fluorescence which may generate significant NIR energy. As yet another example, rod lens assemblies may generate MR energy due to auto-fluorescence. This unwanted NVL may be a similar energy to the emitted NVL from the target area 10 and thus degrade the quality of the image captured by the NVL image sensor 130b. For example, the captured image may be too pronounced, too blurry, too light, too diffuse, and/or too discolored due to the unwanted NVL. In some examples, the endoscopic system 100 reduces the output of the visible light source 110a to reduce the amount of unwanted NVL. However, in some situations, this is either not possible (e.g., when the user manually increases the brightness of the visible light source, when the current use case requires the visible light source to be bright, etc.), is not sufficient (e.g., the amount of unwanted NVL is still significant enough to degrade results), or may confuse the operator (a reflective instrument/device may cause a large VL signal).

The CCU 140 executes (e.g., via the data processing hardware 142 executing instructions stored on the memory hardware 144) an NVL suppressor 150. The NVL suppressor 150 reduces unwanted NVL 114w (i.e., reduces NVL intensity 240) based on, for example, a VL intensity 220. Generally, as the VL intensity 220 of VL 112b increases, the amount of unwanted NVL 114w also increases in a corresponding relationship. That is, as VL intensity 220 increases, an unwanted NVL intensity 222 also increases. This unwanted NVL intensity 222 is a result from unwanted NVL 114w. For example, when a highly visible light-reflective object (e.g., a metallic surgical instrument) enters the field of view of the camera, the intense reflection likely will include increased unwanted NVL 114w. Thus, by measuring the VL intensity 220 captured by each pixel, the NVL suppressor 150 may infer and correct for the amount of unwanted NVL 114w. Because the VL image sensor 130a and the NVL image sensor 130b are co-sited, each sensor 130a, 130b has corresponding pixels that allows the NVL suppressor 150 to establish the relationship between VL intensity 220 and unwanted NVL 114w for the pixels of the NVL image sensor 130b. For example, assuming each image sensor 130a, 130b includes an array of pixels addressable in Cartesian coordinates, pixel (2, 5) (i.e., the second pixel on the x-axis and the fifth pixel on the y-axis of the array) of the VL image sensor 130a corresponds to the pixel (2, 5) of the NVL image sensor 130b. Continuing this example, the pixel (2, 5) of the VL image sensor 130a receives the VL 112a reflected by a portion of the scene (target area 10) while the pixel (2, 5) of the NVL image sensor 130b receives the NVL 114a of the same portion of the scene (target area 10).

In some implementations, a VL measurer 200 receives the VL image data 132 (which may be pre-processed by the CCU 140). For each pixel in the VL image sensor 130a, the VL measurer 200 determines the VL intensity 220 of the VL 112b (e.g., white light) captured by the pixel of the VL image sensor 130a. The VL measurer 200 also determines, based on the VL intensity, an amount of unwanted NIR light captured by the corresponding pixel of the NVL image sensor 130b. In some implementations, the NVL image sensor 130b may be used to measure the unwanted NVL while the VL imaging is occurring and only VL image data 132 is displayed to the operator. The NVL image sensor 130b may collect NIR energy due to the VL light source 110a and other components' (e.g. light guide 116) autofluorescence for use by the NVL suppressor 150. Likewise, in instances of simultaneous VL and NVL image data 132a and 132b being displayed, the NVL light source 110b could be turned off for a short period of time to collect NIR energy.

In some implementations, the VL measurer 200 also determines a threshold 210 for the VL intensity 220 received by the pixel of the VL image sensor 130b. Pixels of the NVL image sensor 130b associated with pixels of the VL image sensor 130a that receive sufficient VL intensity 220 to exceed the threshold 210 may receive correction while pixels of the NVL image sensor 130b associated with pixels of the VL image sensor 130a that do not receive sufficient VL intensity 220 to exceed the threshold 210 may not receive correction. Each threshold 210 may be pre-determined (e.g., set by a user and/or the manufacturer). Additionally or alternatively, the thresholds 210 may be based on a number of parameters such as measured VL 112b (i.e., VL intensity 220) of a scene imaged by the VL image sensor 130a, NVL 114b of a scene imaged by the NVL image sensor 130b, a type of procedure being performed, and/or one or more parameters specific to the endoscopic system 100. For example, an amount of glass of the endoscopic or fluorescence imaging system 100, a type of glass of the endoscopic system 100, a type of adhesive of the fluorescence imaging system, and/or a type of the white light source may impact an amount of auto-fluorescence and thus affect the determined thresholds 210. Each pixel of the VL image sensor 130a may have the same threshold 210, or each pixel may have an individually tailored threshold 210. For example, pixels near the center of the VL image sensor 130a may have different thresholds 210 than pixels near an edge of the VL image sensor 130a. Specific thresholds 210 for a specific endoscopic system 100 may be determined via testing of the specific or similar system by, for example, measuring amounts of NVL 114b imaged by the NVL image sensor 130b when the visible light source 110a is enabled and disabled. It should be appreciated that the look-up table shown in FIG. 2A may be modified to account for the various factors listed above.

An NVL model 300 receives the determined VL intensities 220 and thresholds 210 for each pixel of the VL image sensor 130a. The NVL model 300 determines, for each pixel of the VL image sensor 130a, based on the determined VL intensity 220 and the determined threshold 210 for VL intensity 220 received by the pixel of the VL image sensor 130a, an amount of unwanted NVL 114w (e.g., NIR light) captured by the corresponding pixel of the NVL image sensor 130b. The unwanted NVL 114w originates from sources other than the non-visible light source 110b. For example, the unwanted NVL 114w originates from the visible light source 110a or from auto-fluorescence of the endoscopic system 100 (e.g., from the light guide 114 or other components).

The NVL model 300 reduces an intensity of unwanted NVL 114w in the NVL image data 132b captured by the corresponding pixel of the NVL image sensor 130b based on the determined amount of unwanted NVL 114w, so as to provide accurate image data for each pixel of the infrared image sensor. For example, as discussed in more detail below, the NVL model 300 modifies one or more pixels of the NVL image data 132b to reduce the amount of unwanted NVL 114w. The CCU 140 may combine the adjusted NVL image data 310 (i.e., the NVL image data 132b with reduced unwanted NVL 114w) with the VL image data 132a or otherwise process the image data 132 for displaying on the display 180. The adjusted NVL image data 310 provides a clearer and more accurate representation of the desired NVL 114b (e.g., fluorescence emitted by dye) in the captured NVL image data 132b.

Referring now to FIG. 2A, in some examples, the NVL model 300 may include a lookup table 200 (FIG. 2A). The lookup table 200 may include a plurality of values of different VL intensities 220, each of the plurality of values of VL intensities 220 having an associated amount of unwanted NVL. Thus, the NVL model 300 may determine an NVL correction value 230 to reduce the amount of unwanted NVL captured by the corresponding pixel of the NVL image sensor 130b by obtaining, from the lookup table, the NVL correction value 230 based on the VL intensity 220 received by the pixel of the VL image sensor 130a that corresponds to one of the plurality of values of VL intensity 220. The values of intensity may be measured in units, for example watts per square meter or a sensor output value in digital format which may depend upon the digital resolution of the sensor output value (e.g., 0 to 255, 0 to 4095, etc.). For example, the lookup table 200 may associate the VL intensity 220 of 100 with the NVL correction value 230 of 2. In this example, when the determined VL intensity 220 of the VL 112b at a given pixel is 100, the NVL model 300 may obtain the corresponding NVL correction value 230 (which is associated with the amount of unwanted NVL 114w) of 2 from the lookup table 200, and reduce the value of the corresponding pixel of the NVL image sensor 130b by 2.

In the illustrated example of FIG. 2A, the lookup table 200 includes two columns. The first column includes measured VL intensity values 220 and the second column includes corresponding NVL correction values 230, which is based on the amount of unwanted NVL 114w at that VL intensity 220. That is, the NVL model 300 determines the NVL correction value 230 based on the received VL intensity 220 for each pixel of the VL image sensor 130a. The NVL model 300 may reduce the amount of unwanted NVL 114w based on the NVL correction value 230. Although a single correction value 230 may be used based on the VL intensity value, the correction values could be applied on a pixel-by-pixel basis, i.e. each pixel could have its own correction independent from the others.

Figure 2B:
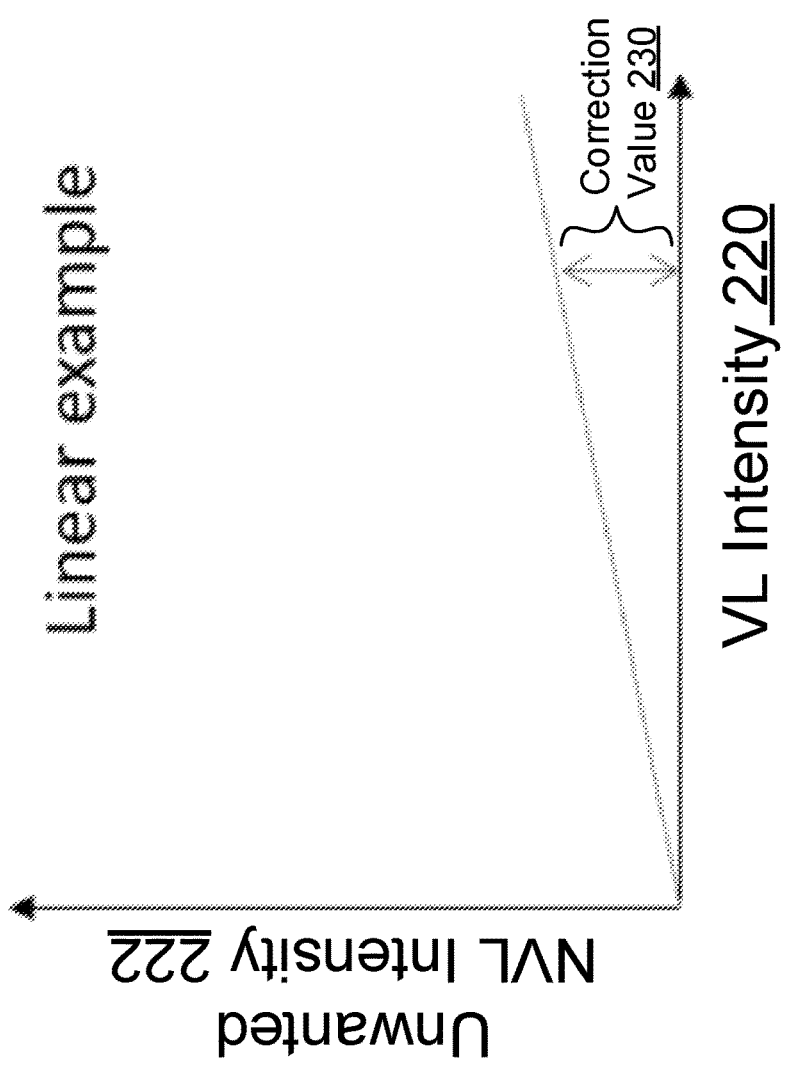
FIGS. 2B and 2C are plots of visible light intensity versus non-visible light intensity.

Referring now to FIG. 2B, plot 250a illustrates a plot of measured VL intensity 220 (x-axis) versus unwanted NVL intensity 222 (y-axis). This plot 250a demonstrates a linear example that, as the VL intensity 220 increases, the unwanted NVL intensity 222 similarly increases. Ideally, the increasing the VL intensity 220 does not increase the unwanted NVL intensity 222, and thus the increase in unwanted NVL intensity 222 includes unwanted NVL 114w. The increase in unwanted NVL intensity 222 thus corresponds to the amount of unwanted NVL 114w and the correction value 230. That is, the increase in unwanted NVL intensity 222 due to the increase in VL intensity 220 may be offset by the NVL correction value 230. The NVL correction values 230 may be determined via empirical means. For example, the NVL correction values 230 may be determined based on measurements of VL intensity 220 and unwanted NVL intensity 222 when the light sources 110a, 110b are enabled and/or disabled. The NVL correction value 230 may reduce the unwanted NVL intensity 222 until NVL 114w does not cause noticeable or significant degradation in the composition image 170. The NVL correction value 230 may be based on a desired or required sensitivity of the system 100 or composition image 170. In some examples, the NVL correction value 230 is based on a saturation level for the pixel (i.e., the pixel's maximum value).

Figure 2C:
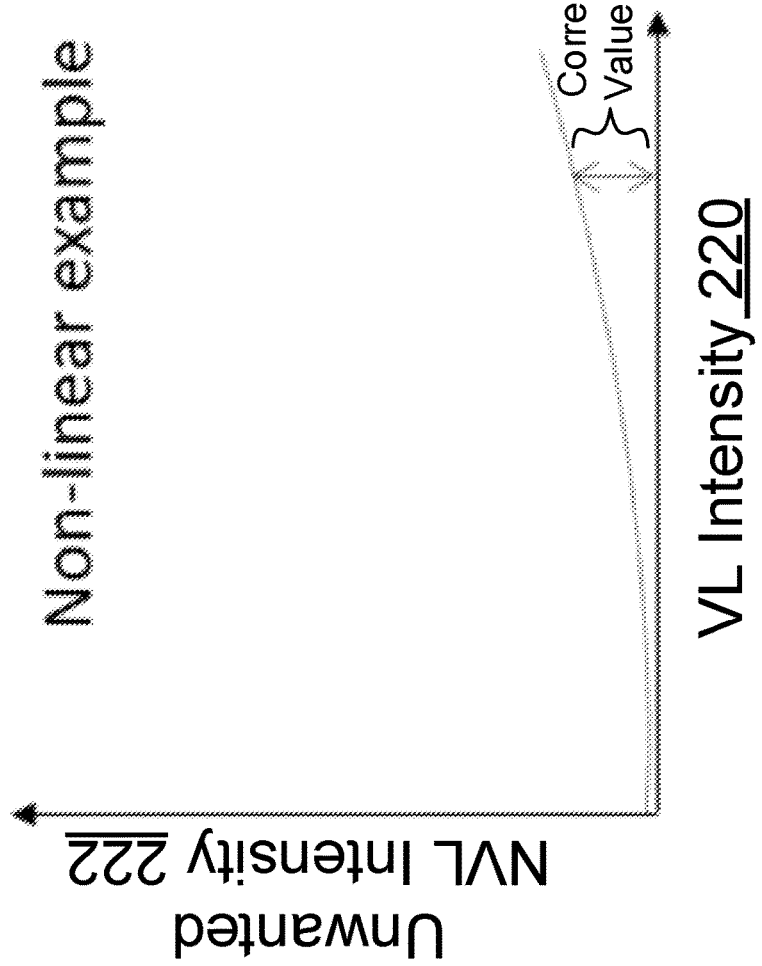

Referring now to FIG. 2C, plot 250b illustrates another plot of measured VL intensity 220 (x-axis) versus unwanted NVL intensity 222 (y-axis). Here, the plot 250b illustrates a non-linear example of the relationship between VL intensity 220 and unwanted NVL intensity 222. That is, while in some examples, the relationship between VL intensity 220 and unwanted NVL intensity 222 is linear (FIG. 2B), in other examples, the relationship between VL intensity 220 and unwanted NVL intensity 222 is non-linear. However, in either case, the correction value 230 (e.g., based on lookup table 200) reduces the NVL intensity to reduce unwanted NVL 114w.

In some implementations, the NVL suppressor 150 reduces the NVL intensity 222 based on the amount that the VL intensity 222 exceeds a threshold for the pixel of the VL image sensor 130a. For example, each pixel of the VL image sensor 130a may have an individual threshold value, and based on the amount that the VL intensity 220 exceeds the threshold for each pixel, the NVL suppressor 150 reduces the NVL intensity. For example, the NVL suppressor 150 may use a lookup table similar to the lookup table 200 to store the thresholds and associated NVL intensity adjustments.

Figure 3:
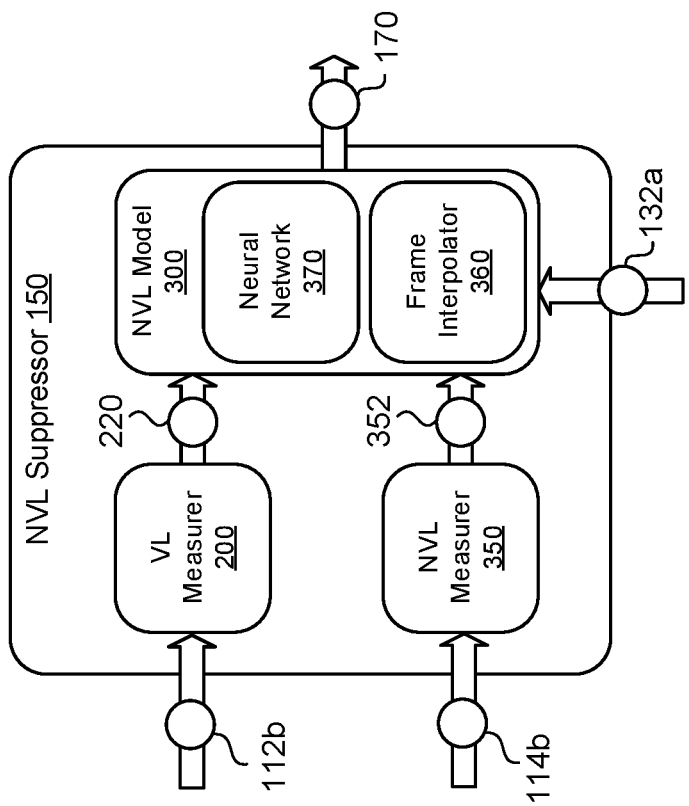
FIG. 3 is a schematic view of a non-visible light suppressor.

Referring now to FIG. 3, in some implementations, the NVL suppressor 150 includes an NVL measurer 350. The NVL measurer 350 may, for each pixel in the NVL image sensor 130b, measure a difference 352 between the NVL intensity received by the pixel of the NVL image sensor 130b when the non-visible light source 110b is enabled and when the visible light source 110a is disabled. With the visible light source 110a disabled, the NVL measurer 350 measures only the NVL intensity (i.e., without unwanted NVL 114w) of the fluorescence as disabling the visible light source 110a may eliminate some or all of the unwanted NVL 114w. Based on the measured difference 352 by the NVL measurer 350, the NVL model 300 may update the threshold 210 and/or correction value 230 for the VL intensity 220 received by the pixel. Another method would include leaving the VL light source on while the NVL light source toggles off periodically (if in use). The correction values could then be calculated directly from the NVL image sensor when the NVL light source is turned off. Yet another method would include calculating correction values during a white balance operation, prior to use in surgery. Here, the results may not be as accurate but could be used to obtain a spatial distribution of correction values, such as center pixels being weighted differently than perimeter pixels.

Thus, in some implementations, the NVL model 300 may update the thresholds 210 and/or correction values 230 based on actual measurements of desired NVL 114b. Because changes of the scene may lead to different amounts of wanted and unwanted NVL 114b, the NVL measurer 350 may periodically update the measured difference 352. For example, the NVL measurer may update the difference 352 once a second, ten times a second, etc. The frequency may be configurable (e.g., by a user of the system 100) or automated depending on the surgical scene.

When the NVL measurer 350 measures the NVL intensity, the NVL suppressor may disable the visible light source 110a for only a short period of time (e.g., one frame) in order to minimize impact to the illumination of the scene. In some examples, the system 100 may include a frame interpolator 360 to interpolate frames of VL image data 132a based on previous image data to replace frames missing when the visible light source 110a is disabled or alternately freeze the pervious image data for reuse in a subsequent frame. Optionally, the NVL suppressor 150 may disable the visible light source 110a only when the scene is relatively static and unchanging (i.e., the camera is not moving) so as to increase the accuracy of the frame interpolator 360. That is, when the scene is unchanging, the frame interpolator 360 may more accurately interpolate frames of image data, and thus the NVL suppressor 150 may wait until there is less than a threshold amount of change in image data detected by the image sensors between frames prior to disabling the visible light source 110a to measure the intensity of the NVL 114b.

In some examples, the NVL model determines correction value 230 for the VL intensity 220 received by each pixel of the VL image sensor 130a by processing the VL image data 132a and the NVL image data 132b based on a geometry of a the scene captured by the camera head unit 102. For example, the NVL model 300 may include a neural network 370 that is trained to determine the amount of unwanted NVL 114w based on the geometry of the scene and the VL image data 132a and the NVL image data 132b. The neural network 370 may be trained using supervised learning methods and annotated frames of image data that indicate the ground truth amount of unwanted NVL. The neural network 370 may also train the NVL model 300 using unsupervised learning methods and unannotated frames of image data or any combination supervised and unsupervised methods.

In some examples, the NVL suppressor 150 controls the visible light source 110a to minimize the amount of unwanted NVL 114w. For example, the NVL suppressor 150 reduces the output of the visible light source 110a to a minimal amount acceptable for the current use case. The NVL suppressor 150 may automatically adjust the brightness of the visible light source 110a based on processing of the VL image data 132a. For example, the NVL suppressor 150 may base the brightness of the visible light source 110a based on intensities measured by the VL measurer 200.

Figure 4:
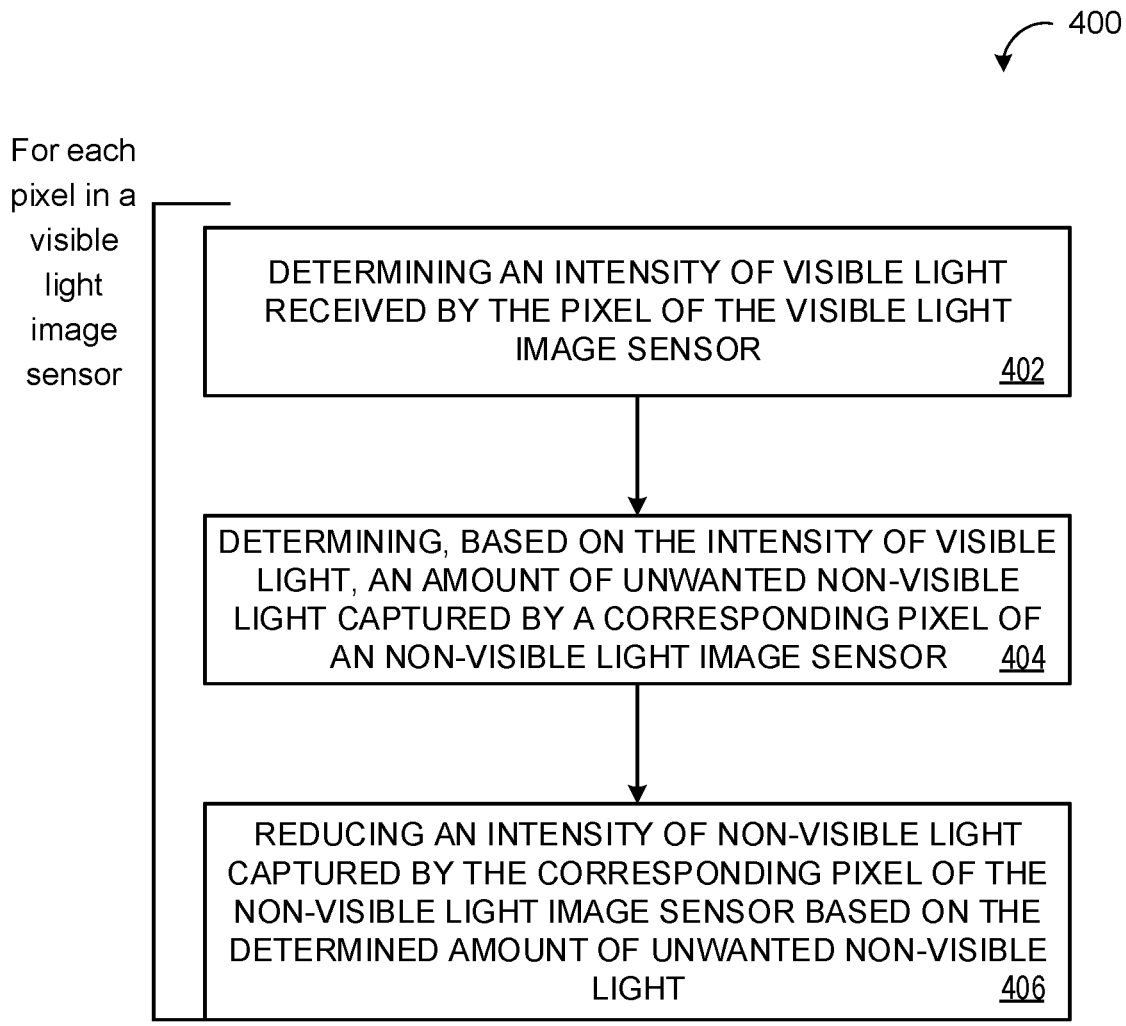
FIG. 4 a flowchart of an example method for suppressing unwanted non-visible light in an imaging system.

FIG. 4 is a flowchart of example operations 400 for an endoscopic system or a fluorescence imaging system 100 that is configured to generate a video image onto a display 180. The system 100 includes a visible light source 110a (e.g., a white light source) for emitting visible light 112b (e.g., white light). The system 100 also includes a non-visible light source 110b (e.g., an infrared light source) for emitting non-visible light (e.g., infrared light). The system 100 includes a non-visible light image sensor 130b for capturing infrared image data in a non-visible light spectrum and a visible light image sensor for capturing visible light image data in the visible light spectrum. Each pixel of the visible light image sensor corresponds to a pixel of the non-visible light image sensor.

The system 100 includes data processing hardware 142 in communication with the non-visible light image sensor 130b and the visible light image sensor 130a. The system 100 also includes memory hardware 144 in communication with the data processing hardware 142. The memory hardware stores instructions that when executed on the data processing hardware 142 cause the data processing hardware to perform operations. The operations include, at step 402, for each pixel in the visible light image sensor 130a, determining a VL intensity 220 of visible light received by the pixel of the visible light image sensor 130a.

At step 404, the operations include determining, based on the VL intensity 220 of visible light received by the pixel of the visible light image sensor 130a, an amount of unwanted non-visible light 114w (e.g., near-infrared light) captured by the corresponding pixel of the non-visible light image sensor 130b. The unwanted non-visible light 114w originates from sources other than the non-visible light source 110b. At step 406, the operations include reducing an intensity of non-visible light in the non-visible light image data 132b captured by the corresponding pixel of the non-visible light image sensor 130b based on the determined amount of unwanted non-visible light 114w, so as to provide accurate image data for each pixel of the non-visible light image sensor 130b.

Figure 5:
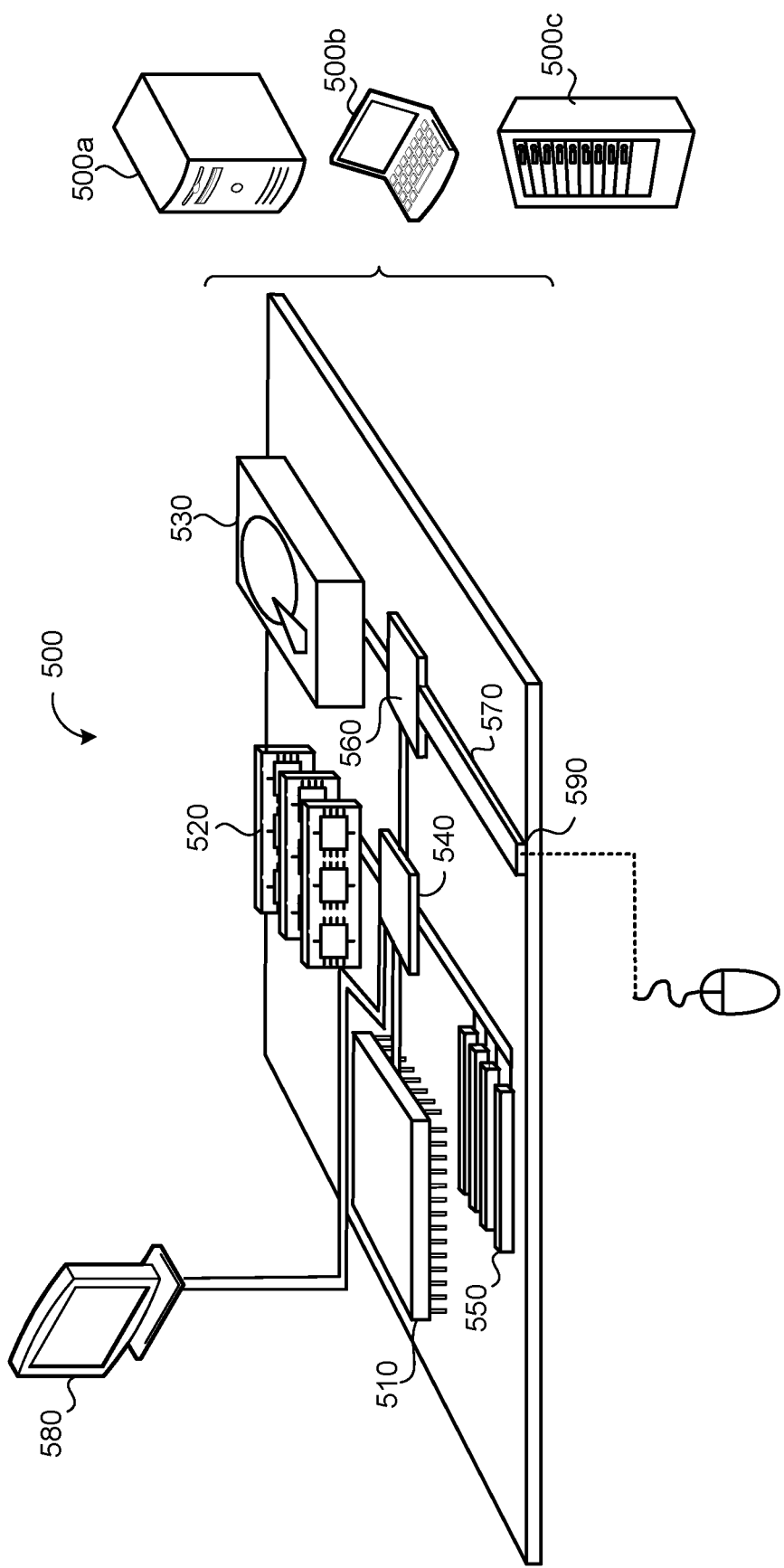
FIG. 5 is a schematic view of an example computing device that may be used to implement the systems and methods described herein.

FIG. 5 is schematic view of an example computing device 500 (e.g., data processing hardware 142 and memory hardware 144) that may be used to implement the systems and methods described in this document. For examples, computing device 500 may perform tasks such as controlling the light source 50 (e.g., enabling and disabling the light source, switching between visible light and non-visible light, etc.), configuring and communicating with the image sensors 130 (e.g., receiving the image data), and implementing and executing one or more components 200, 300, 400, 500 of the system 100. In some examples, the computing device 500 transmits image data to the display 180. That is, using the data received from the image sensors 130, the computing device 500 may store and execute instructions or operations to implement components 200, 300, 400, 500, etc. The computing device 500 is intended to represent various forms of digital computers, such as laptops, desktops, workstations, personal digital assistants, servers, blade servers, mainframes, and other appropriate computers. The components shown here, their connections and relationships, and their functions, are meant to be exemplary only, and are not meant to limit implementations of the disclosures described and/or claimed in this document.

The computing device 500 (e.g., data processing hardware 142) includes a processor 510, memory 520, a storage device 530, a high-speed interface/controller 540 connecting to the memory 520 and high-speed expansion ports 550, and a low speed interface/controller 560 connecting to a low speed bus 570 and a storage device 530. Each of the components 510, 520, 530, 540, 550, and 560, are interconnected using various busses, and may be mounted on a common motherboard or in other manners as appropriate. The processor 510 can process instructions for execution within the computing device 500, including instructions stored in the memory 520 or on the storage device 530 to display graphical information for a graphical user interface (GUI) on an external input/output device, such as display 580 coupled to high-speed interface 540. In other implementations, multiple processors and/or multiple buses may be used, as appropriate, along with multiple memories and types of memory. Also, multiple computing devices 500 may be connected, with each device providing portions of the necessary operations (e.g., as a server bank, a group of blade servers, or a multi-processor system).

The memory 520 stores information non-transitorily within the computing device 500. The memory 520 may be a computer-readable medium, a volatile memory unit(s), or non-volatile memory unit(s). The non-transitory memory 520 may be physical devices used to store programs (e.g., sequences of instructions) or data (e.g., program state information) on a temporary or permanent basis for use by the computing device 500. Examples of non-volatile memory include, but are not limited to, flash memory and read-only memory (ROM)/programmable read-only memory (PROM)/erasable programmable read-only memory (EPROM)/electronically erasable programmable read-only memory (EEPROM) (e.g., typically used for firmware, such as boot programs). Examples of volatile memory include, but are not limited to, random access memory (RAM), dynamic random access memory (DRAM), static random access memory (SRAM), phase change memory (PCM) as well as disks or tapes.

The storage device 530 is capable of providing mass storage for the computing device 500. In some implementations, the storage device 530 is a computer-readable medium. In various different implementations, the storage device 530 may be a floppy disk device, a hard disk device, an optical disk device, or a tape device, a flash memory or other similar solid state memory device, or an array of devices, including devices in a storage area network or other configurations. In additional implementations, a computer program product is tangibly embodied in an information carrier. The computer program product contains instructions that, when executed, perform one or more methods, such as those described above. The information carrier is a computer- or machine-readable medium, such as the memory 520, the storage device 530, or memory on processor 510.

The high speed controller 540 manages bandwidth-intensive operations for the computing device 500, while the low speed controller 560 manages lower bandwidth-intensive operations. Such allocation of duties is exemplary only. In some implementations, the high-speed controller 540 is coupled to the memory 520, the display 580 (e.g., through a graphics processor or accelerator), and to the high-speed expansion ports 550, which may accept various expansion cards (not shown). In some implementations, the low-speed controller 560 is coupled to the storage device 530 and a low-speed expansion port 590. The low-speed expansion port 590, which may include various communication ports (e.g., USB, Bluetooth, Ethernet, wireless Ethernet), may be coupled to one or more input/output devices, such as a keyboard, a pointing device, a scanner, or a networking device such as a switch or router, e.g., through a network adapter.

The computing device 500 may be implemented in a number of different forms, as shown in the figure. For example, it may be implemented as a standard server 500*a* or multiple times in a group of such servers 500*a*, as a laptop computer 500*b*, or as part of a rack server system 500*c*.

Various implementations of the systems and techniques described herein can be realized in digital electronic and/or optical circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor and can be implemented in a high-level procedural and/or object-oriented programming language, and/or in assembly/machine language. As used herein, the terms "machine-readable medium" and "computer-readable medium" refer to any computer program product, non-transitory computer readable medium, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term "machine-readable signal" refers to any signal used to provide machine instructions and/or data to a programmable processor.

The processes and logic flows described in this specification can be performed by one or more programmable processors, also referred to as data processing hardware, executing one or more computer programs to perform functions by operating on input data and generating output. The processes and logic flows can also be performed by special purpose logic circuitry, e.g., an FPGA (field programmable gate array) or an ASIC (application specific integrated circuit). Processors suitable for the execution of a computer program include, by way of example, both general and special purpose microprocessors, and any one or more processors of any kind of digital computer. Generally, a processor will receive instructions and data from a read only memory or a random access memory or both. The essential elements of a computer are a processor for performing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Computer readable media suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto optical disks; and CD ROM and DVD-ROM disks. The processor and the memory can be supplemented by, or incorporated in, special purpose logic circuitry.

To provide for interaction with a user, one or more aspects of the disclosure can be implemented on a computer having a display device, e.g., a CRT (cathode ray tube), LCD (liquid crystal display) monitor, or touch screen for displaying information to the user and optionally a keyboard and a pointing device, e.g., a mouse or a trackball, by which the user can provide input to the computer. Other kinds of devices can be used to provide interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's client device in response to requests received from the web browser.

While particular embodiments have been illustrated and described herein, it should be understood that various other changes and modifications may be made without departing from the spirit and scope of the claimed subject matter. Moreover, although various aspects of the claimed subject matter have been described herein, such aspects need not be utilized in combination. It is therefore intended that the appended claims cover all such changes and modifications that are within the scope of the claimed subject matter.

The invention claimed is:

1. An imaging system for use in a medical procedure, the imaging system configured to generate a video image onto a display, the imaging system comprising:
   a first light source for emitting illuminating light;
   an second light source for emitting excitation light;
   a first image sensor for capturing first image data in the visible spectrum;
   a second image sensor for capturing second image data in the non-visible spectrum, each pixel of the first image sensor corresponding to a pixel of the second image sensor;
   data processing hardware in communication with the first image sensor and the second image sensor; and
   memory hardware in communication with the data processing hardware, the memory hardware storing instructions that when executed on the data processing hardware cause the data processing hardware to perform operations comprising:
   for each pixel in the first image sensor:
      determining an intensity of visible light received by the pixel of the first image sensor;
      determining, based on the intensity of visible light received by the pixel of the first image sensor, an amount of unwanted non-visible light captured by the corresponding pixel of the second image sensor, the unwanted non-visible light originating from sources other than the second light source; and
      reducing an intensity of non-visible light in the second image data captured by the corresponding pixel of the second image sensor based on the determined amount of unwanted non-visible light, so as to provide accurate image data for each pixel of the second image sensor.

2. The imaging system of claim 1, wherein the operations further comprise determining a threshold for the intensity of visible light received by the pixel of the first image sensor, and wherein determining the amount of unwanted non-visible light captured by the corresponding pixel of the second image sensor is based on the threshold for the intensity of visible light received by the pixel of the first image sensor.

3. The imaging system of claim 2, wherein determining the amount of unwanted non-visible light captured by the corresponding pixel of the second image sensor comprises determining an amount that the intensity of visible light exceeds the threshold for the pixel of the first image sensor.

4. The imaging system of claim 3, wherein reducing the intensity of the non-visible light in the non-visible light image data captured by the corresponding pixel of the second image sensor based on the determined amount of unwanted non-visible light comprises reducing the intensity of non-visible light in the non-visible light image data captured by the corresponding pixel of the second image sensor based on the amount that the intensity of visible light exceeds the threshold for the pixel of the first light image sensor.

5. The imaging system of claim 2, wherein the threshold for the intensity of visible light received by the pixel of the first image sensor is at a saturation level.

6. The imaging system of claim 2, wherein the threshold for the intensity of visible light received by the pixel of the first image sensor is based on at least one parameter of the fluorescence imaging system.

7. The imaging system of claim 6, wherein the at least one parameter comprises at least one selected from the group consisting of (i) an amount of glass of the imaging system, (ii) a type of glass of the imaging system, (iii) a type of adhesive of the imaging system, and (iv) a type of the first light source.

8. The imaging system of claim 2, wherein determining the threshold for the intensity of visible light received by the pixel of the first image sensor comprises processing, using a model, the non-visible light image data and the visible light image data based on a scene geometry of a scene captured by the imaging system.

9. The imaging system of claim 8, wherein the model is a neural network.

10. The imaging system of claim 2, wherein the operations further comprise, for each pixel in the second image sensor:
   measuring a difference between the intensity of non-visible light received by the pixel of the second image sensor when the second light source is enabled and when the first light source is disabled; and updating the determined threshold for the intensity of visible light received by the pixel of the first image sensor based on the measured difference.

11. The imaging system of claim 1, further including a lookup table, the lookup table having a plurality of values of visible light intensity, each of the plurality of values of visible light intensities having an associated amount of unwanted non-visible light, wherein determining the amount of unwanted non-visible light captured by the corresponding pixel of the second image sensor comprises obtaining, from the lookup table, the amount of unwanted non-visible light based on the intensity of visible light received by the pixel of the first image sensor that corresponds to one of the plurality of values of visible light intensity.

12. The imaging system of claim 1, wherein reducing the intensity of non-visible light captured by the corresponding pixel of the second image sensor based on the determined amount of unwanted non-visible light comprises reducing the intensity of non-visible light received by the corresponding pixel of the infrared image sensor proportionally based on the intensity of visible light received by the pixel of the first image sensor.

13. The imaging system of claim 1, wherein the first image sensor and the second image sensor are co-sited.

14. A method for suppressing unwanted non-visible light in an imaging system comprising a first light source, a second light source, a first image sensor configured to capture visible light image data, and a second image sensor configured to capture non-visible light image data, each pixel of the first light image sensor corresponding to a pixel of the second image sensor, the imaging system configured to generate a video image to a display, the method comprising:

for each pixel in the first image sensor:
    determining an intensity of visible light received by the pixel of the first image sensor;
    determining, based on the intensity of visible light received by the pixel of the first image sensor, an amount of unwanted non-visible light captured by the corresponding pixel of the second image sensor, the unwanted non-visible light originating from sources other than the second light source; and
    reducing an intensity of unwanted non-visible light in the non-visible light image data captured by the corresponding pixel of the second image sensor based on the determined amount of unwanted non-visible light, so as to provide accurate image data for each pixel of the second image sensor.

15. The method of claim 14, further comprising determining a threshold for the intensity of visible light received by the pixel of the first image sensor, and wherein determining the amount of unwanted non-visible light captured by the corresponding pixel of the second image sensor is based on the threshold for the intensity of visible light received by the pixel of the first image sensor.

16. The method of claim 15, wherein determining the amount of unwanted non-visible light captured by the corresponding pixel of the second image sensor comprises determining an amount that the intensity of visible light exceeds the threshold for the pixel of the first image sensor.

17. The method of claim 16, wherein reducing the intensity of the non-visible light in the non-visible image data captured by the corresponding pixel of the second image sensor based on the determined amount of unwanted non-visible light comprises reducing the intensity of non-visible light in the non-visible light image data captured by the corresponding pixel of the second image sensor based on the amount that the intensity of visible light exceeds the threshold for the pixel of the first image sensor.

18. The method of claim 15, wherein determining the threshold for the intensity of visible light received by the pixel of the first image sensor comprises processing, using a model, the non-visible light image data and the visible light image data based on a scene geometry of a scene captured by the imaging system.

19. The method of claim 18, wherein the model is a neural network.

20. The method of claim 15, wherein the threshold for the intensity of visible light received by the pixel of the first image sensor is at a saturation level.

21. The method of claim 15, wherein the threshold for the intensity of visible light received by the pixel of the first image sensor is based on at least one parameter of the imaging system.

22. The method of claim 21, wherein the at least one parameter comprises at least one selected from the group consisting of (i) an amount of glass of the imaging system, (ii) a type of glass of the imaging system, (iii) a type of adhesive of the imaging system, and (iv) a type of the first light source.

23. The method of claim 15, further comprising, for each pixel in the second image sensor:
    measuring a difference between the intensity of non-visible light received by the pixel of the second image sensor when the second light source is enabled and when the first light source is disabled; and
    updating the determined threshold for the intensity of visible light received by the pixel of the first light image sensor based on the measured difference.

24. The method of claim 14, further including a lookup table, the lookup table having a plurality of values of visible light intensity, each of the plurality of values of visible light intensities having an associated amount of unwanted non-visible light, wherein determining the amount of unwanted non-visible light captured by the corresponding pixel of the second image sensor comprises obtaining, from the lookup table, the amount of unwanted non-visible light based on the intensity of visible light received by the pixel of the first image sensor that corresponds to one of the plurality of values of visible light intensity.

25. The method of claim 14, wherein reducing the intensity of non-visible light captured by the corresponding pixel of the second image sensor based on the determined amount of unwanted non-visible light comprises reducing the intensity of non-visible light received by the corresponding pixel of the second image sensor proportionally based on the intensity of visible light received by the pixel of the first image sensor.

26. The method of claim 14, wherein the first image sensor and the second image sensor are co-sited.

* * * * *